(12) United States Patent
Kan et al.

(10) Patent No.: US 7,053,439 B2
(45) Date of Patent: May 30, 2006

(54) CHEMORECEPTIVE SEMICONDUCTOR STRUCTURE

(76) Inventors: Edwin Kan, 22 Beckett Way, Ithaca, NY (US) 14850; Bradley A. Minch, 15 Marcy Ct., Ithaca, NY (US) 14850-9480

( * ) Notice: Subject to any disclaimer, the term of this patent is extended or adjusted under 35 U.S.C. 154(b) by 0 days.

(21) Appl. No.: 10/695,432

(22) Filed: Oct. 28, 2003

(65) Prior Publication Data

US 2004/0256655 A1 Dec. 23, 2004

Related U.S. Application Data

(60) Provisional application No. 60/422,014, filed on Oct. 29, 2002.

(51) Int. Cl.
*H01L 29/788* (2006.01)
(52) U.S. Cl. .................. 257/315; 257/239; 257/414
(58) Field of Classification Search .............. 257/239, 257/261, 315, 321, 414
See application file for complete search history.

(56) References Cited

U.S. PATENT DOCUMENTS

| | | | | |
|---|---|---|---|---|
| 4,232,326 | A | | 11/1980 | Neidig et al. ............... 257/253 |
| 4,397,714 | A | * | 8/1983 | Janata et al. ............... 205/775 |
| 4,437,969 | A | | 3/1984 | Covington et al. ......... 257/253 |
| 4,636,827 | A | | 1/1987 | Rudolf ...................... 257/253 |
| 4,728,882 | A | * | 3/1988 | Stanbro et al. ............. 324/687 |
| 5,071,770 | A | | 12/1991 | Kolesar, Jr. ................ 436/151 |
| 5,719,520 | A | * | 2/1998 | Au et al. .................... 327/427 |
| 2002/0117659 | A1 | | 8/2002 | Lieber et al. ............... 257/14 |

OTHER PUBLICATIONS

Bergveld, P., "A Critical Evaluation of Direct Electrical Protein Detection Methods", *Biosensors & Bioelectronics*, 6, (1991), 55-72.

Bergveld, P., "Development of an Ion-Sensitive Solid-State Device for Neurophysiological Measurements", *IEEE Trans. Biomedical Engineering, BME-17* (1), (1970), 70-71.

Boahen, K. A., "The Retinomorphic Approach: Pixel Parallel Adaptive Amplification, Filtering, and Amplification", *In: Neuromorphic Systems Engineering: Neural Networks in Silicon*, T.S. Lande, Ed., Boston: Kluwer,(1998), 129-150.

Colapicchioni, C., et al., "Immunienzymatic Assay Using CHEMFET Devices", *Sensors and Actuators B: Chemical*, 4(3-4), (Jun. 1991), 245-250.

Dewa, A. S., et al., "Biosensors", *In: Semiconductor Sensors, Chapter 9*, Edited by S.M. Sze. John Wiley and Sons,(1994), 425-472.

(Continued)

*Primary Examiner*—Allan R. Wilson
(74) *Attorney, Agent, or Firm*—Schwegman, Lundberg, Woessner and Kluth P.A.

(57) ABSTRACT

A field effect transistor has a floating gate with an extended portion. A selectively chemoreceptive finger or layer is electrostatically coupled to the extended portion of the floating gate, and induces a voltage on the gate in response to selected chemicals or other conditions affecting the finger. The voltage on the gate modulates current flowing between a source and a drain of the transistor, effectively sensing the presence of the selected chemicals or conditions. In one embodiment, multiple chemoreceptive fingers are electrostatically coupled to the extended portion of the floating gate. In a further embodiment, an array of such field effect transistors provide a sensor for multiple conditions.

13 Claims, 5 Drawing Sheets

OTHER PUBLICATIONS

Diorio, C., et al., "A Complementary Pair of Four-Terminal Silicon Synapses", *Analog Integrated Circuits and Signal Processing*, 13 (1-2), (1997), 153-166.

Diorio, C., et al., "A Floating-Gate MOS Learning Array with Locally Computed Weight Updates", *IEEE Transactions on Electron Devices*, 44 (12), (Dec. 1997), 2281-2289.

Diorio, C., et al., "Floating-Gate MOS Synapse Transistors", *In: Neuromorphic Systems Engineering: Neural Networks in Silicon*, T.S. Lande, Ed., Boston: Kluwer,(1998), 315-338.

Fragniere, E., et al., "An Analogue VLSI Model of Active Cochlea", *In; Neuromorphic Systems Engineering: Neural Networks in Silicon*, T.S. Lande, Ed., Boston: Kluwer,(1998), 19-48.

Grodzinksy, A. J., et al., "Electrokinetic Separations", *In: Biotechnology: a multi-volume comprehensive treatise, 2nd Ed.*, vol. 3, H J Rehm; Gerald Reed; A Puhler; P Stadler; H Sahm—Authors; Cambridge : VCH.,(1993), 680-693.

Hasler, Paul, et al., "Adaptive Circuits and Synapses using pFET Floating-Gate Devices", *In: Learning on Silicon: adaptive VLSI neural systems*, G. Cauwenberghs and M. Bayoumi, Eds., Boston: Kluwer,(1999), 33-65.

Hasler, P., et al., "Floating-Gate Devices: They Are Not Just for Digital Memories Anymore", *ISCAS'99. Proceedings of the 1999 IEEE International Symposium on Circuits and Systems VLSI*, (Jun. 1999), 388-391.

Hermans, E.C. M., "CO, CO/sub 2/CH/sub 4/ and H/sub 2O sensing by polymer covered interdigitated electrode structures", *Sensors and Actuators*, 5(3), (May 1984), 181-186.

Kan, E. C., et al., "Si Fleas: Technology Demonstration of Functional Modules in Submillimeter Autonomous Microsystems", *Invited Talk, Ninth Foresight Conference on Molecular Nanotechnology*, Santa Clara, CA,(Nov. 9-11, 2001).

Kruger, W. F., et al., "An Adaptive WTA Using Floating-Gate Technology", *In; Advances in Neural Information Processing Systems9*, M.C. Mozer, et al, Eds., London: MIT Press,(1997), 720-726.

Leman, E S., et al., "Characterization of the nuclear matrix proteins in a transgenic mouse model for prostate cancer", *Journal of Cellular Biochemistry*; 86(2), (2002), 203-212.

Liu, Z., et al., "Eluding metal contamination in CMOS front-end fabrication by nanocrystal formation process", *Self-Assembly Processes in Materials. Symposium (Mater. Res. Soc. Proceedings*, vol. 707, (2002), 199-204.

Liu, S C., et al., "Homeostasis in a Silicon Integrate-and-Fire Neuron", *In: Advances in Neural Information Processing Systems 13*, T.K. Leen, et al., Eds., London: MIT Press,(2001), 727-733.

Liu, Zengtao, et al., "Novel Electrostatic Repulsion Forces in MEMS Applications by Nonvolatile Charge Injection", *The Fifteenth IEEE International Conference on Micro Electro Mechanical Systems*, (2002), 598-601.

Liu, Zengtao, et al., "Process and device characteristics of self-assembled metal nano-crystal EEPROM", *Superlattice and Microstructures*, 28 (5-6), (Nov. 2000), 393-399.

Ma, T. P., "Making Silicon Nitride film a Viable Gate Dielectric", *IEEE Transactions On Electron Devices*, 45(3), (Mar. 1998), 680-690.

Mead, C., "Neuromorphic Electronic Systems", *Proceedings of the IEEE*,78(10), (Oct. 1990), 1629-1636.

Minch, Bradley A., et al., "A Floating-Gate Technology for Digital CMOS Processes", *ISCAS '99. Proceedings of the 1999 IEEE International Symposium on Circuits and Systems*, (Jun. 1999), 400-403.

Minch, Bradley A., "A Folded Floating-Gate Differential Pair for Low-Voltage Applications", *The 2000 IEEE International Symposium on Circuits and Systems, Proceedings. ISCAS 2000 Geneva*. vol.: 4, (May 2000), 253-256.

Minch, B. A., et al., "A Silicon Axon", *In: Advances in neural information processing systems 7*, Authors—Gerald Tesauro; David S Touretzky; Todd Leen; Cambridge, Mass. : MIT Press,(1995), 739-746.

Minch, Bradley A., et al., "A vMOS Soft-Max Current Mirror", *1995 IEEE International Symposium on Circuits and Systems, ISCAS '95.*, vol.: 3, (May 1995), 2249-2252.

Minch, Bradley A., "Evolution of a Folded Floating-Gate Differential Pair", *Proceedings of the 43rd IEEE Midwest Symposium on Circuits and Systems*, vol. 3, (May 2000), 1052-1056.

Minch, B. A., "Multiple-Input Translinear Element Log-Domain Filters", *IEEE Transactions on Circuits and Systems II*, 48(1), (Jan. 2001), 29-36.

Minch, B. A., et al., "Multiple-Input Translinear Element Networks", *IEEE Transactions on Circuits and Systems II*, 48(1), (Jan. 2001), 20-28.

Minch, B. A., et al., "Translinear Circuits Using Subthreshold Floating-Gate MOS Transistors", *Analog Integrated Circuits and Signal Processing*, 9(2), (1996), 167-179.

Neuberger, R., et al., "High-electron mobility AlGaN/GaN transistors (HEMTs) for fluid monitoring applications", *Physica Status Solidi A*, 185(1), (May 2001), 85-89.

Rabaey, Jan M., et al., "Designing Memory and Array Structures", *In: Digital Integrated Circuits: a design perspective*, Upper Saddle River, N.J. : Prentice Hall,(1996), 551-628.

Sarpeshkar, R., et al., "A Low-Power Wide-Dynamic-Range Analog VLSI Cochlea", *In: Neuromorphic Systems Engineering: Neural Networks in Silicon*, T.S. Lande, etal, Eds. Boston: Kluwer,(1998), 49-104.

Schalwig, J., et al., "Goup-III-nitride based gas sensing devices", *Physica Status Solidi A*, 185(1), (May 2001), 39-45.

Shepherd, Gordon M., et al., "Olfactory Bulb", *In: The Synaptic Organization of the Brain*, G.M. Shepherd, Ed. 3rd ed., New York: Oxford University Press,(1990), 133-169.

Shibata, T., et al., "A Functional MOS Transistor Featuring Gate-Level Weighted Sum and Threshold Operations", *IEEE Transactions on Electron Devices*, 39(6), (1992), 1444-1455.

Siu, W. M., et al., "Basic Properties of the Electrolyte-SiO2-Si System: Physical and Theoretical Aspects", *IEEE Transactions on Electron Devices, ED-26* (11), (1979), 1805-1815.

Steiner, F. P., et al., "Polymer Coated Capacitive Microintegrated Gas Sensor", *8th International Conference on Solid-State Sensors and Actuators and Eurosensors IX. Digest of Technical Papers*, (Jun. 1995), 814-817.

Yamamoto, T., et al., "An Integrated Temperature and Humidity Sensor", *Proc. Transducers'87*, Tokyo, Japan,(Jun. 1987), 658-660.

\* cited by examiner

CHEMORECEPTIVE SEMICONDUCTOR STRUCTURE

RELATED APPLICATIONS

This application claims priority from U.S. Provisional Application No. 60/422,014; filed on Oct. 29, 2002; which is incorporated herein by reference.

GOVERNMENT FUNDING

The invention described herein was made with U.S. Government support under Grant Number ECS-0210743 awarded by Nanoscale Exploratory Research (NER) and Grant Number R830902 awarded by the National Center for Environmental Research (NCER). The United States Government has certain rights in the invention.

FIELD OF THE INVENTION

The present invention relates to sensors, and in particular to a chemoreceptive semiconductor structure.

BACKGROUND OF THE INVENTION

Chemical and molecular sensing with solid-state devices have involved various approaches including microelectrode, microcalorimeter, acoustic wave devices, chemiresistors, chemicapacitors, chemomechanical sensors, and field effect transistor (FET) based sensors. Many attempts of forming sensors with complementary metal-oxide-silicon (MOS) devices have also been made. Although sensitivity is high in a controlled environment, the devices are limited by sensing selectivity, contamination induced long-term drift in MOS characteristics, and system integration.

SUMMARY OF THE INVENTION

A field effect transistor has a floating gate with an extended portion. A selectively receptive finger is electrostatically coupled to the extended portion of the floating gate, and induces a voltage on the gate in response to selected chemicals or other conditions affecting the finger. The voltage on the gate modulates current flowing between a source and a drain of the transistor, effectively sensing the presence of the selected chemicals.

In one embodiment, multiple chemoreceptive fingers are electrostatically coupled to the extended portion of the floating gate. Each chemoreceptive finger is electrically isolated from the extended portion of the floating gate such as by a nitride plug. In one embodiment, the fingers are referred to as control gates. The floating gate voltage is established through charge sharing or capacitive voltage division, as a weighted sum of the voltages applied to the control gates. The weight on each control gate is proportional to the capacitance of the gate, and is normalized by the total capacitance of the floating gate.

In a further embodiment, and array of such field effect transistors forms a sensor for detecting one or more conditions. An optional independent power source and transmitter provide for remote location of such arrays.

DETAILED DESCRIPTION

In the following description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

Figure 1:
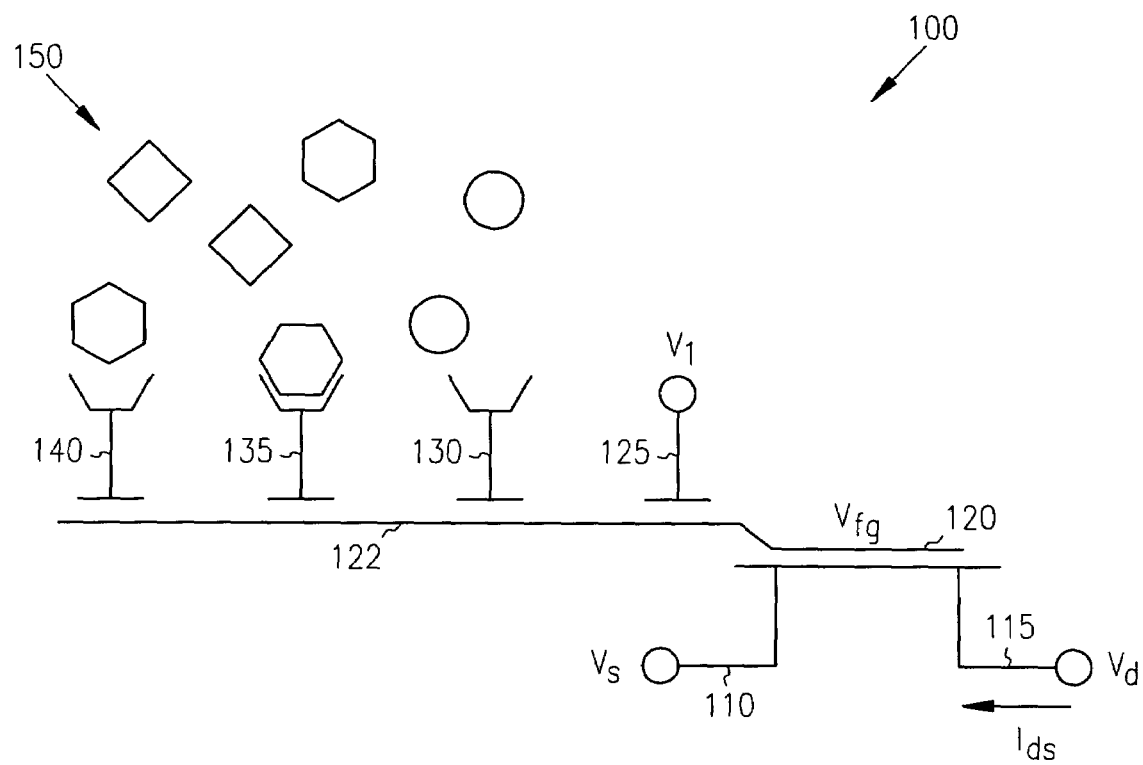
FIG. 1 is a block schematic diagram representing a floating gate transistor having a plurality of control gates, some of which are chemoreceptive.

A four-input neuron metal oxide semiconductor (MOS) (vMOS) transistor is shown in block schematic form at 100 in FIG. 1. Transistor 100 comprises a source 110 and drain 115, and a gate 120 that modulates current flowing between the source and drain. Gate 120 is extended as indicated at 122. Several control gates 125, 130, 135, and 140 are coupled to the extended area 122 of gate 120. The control gates are capacitively coupled in one embodiment to the extended area 122 of gate 120.

In one embodiment, the control gates 130, 135 and 140 comprise fingers that are coated with a chemoreceptive material, while control gate 125 is a normal vMOS control gate. The chemoreceptive material is selective in one embodiment, such that one targeted chemicals as shown generally at 150 bond with the material, creating a charge on the control gate that is capacitively coupled to the floating gate 120.

A floating gate voltage is established through charge sharing or capacitive voltage division, as a weighted sum of the voltages applied to the control gates. The weight on each control gate is directly proportional to that control gate's capacitance and is normalized by the total capacitance of the floating gate.

In one embodiment fewer, or more control gates are provided, and the extended area of the floating gate is formed sufficient to capacitively couple to such number of control gates. Not all the control gates need have chemoreceptive fingers, and the chemicals 150 such fingers are receptive to may be varied on the same transistor 100.

Transconductance gains of each control gate are selected via the control gate capacitances. Because the control gates perform their voltage summation by capacitive voltage division, operation of the transistor may be performed with very little power consumption. Since only the control gate capacitances are charged, there is little or no static power consumption as there is in prior resistive voltage division based devices.

In one embodiment, a normal MOS transistor is constructed. Instead of placing a second-level polysilicon electrode above an area of the floating gate, an opening in the oxide over the gate is constructed, extending through a passivation later all the way down to the floating gate. A thin layer of insulator is formed over the opening. On top of the insulator, a variety of thin films may be deposited to form a chemoreceptive control gate. The properties of the thin films determine a molecular/chemoreceptive property for the chemoreceptive control gate. Any CMOS technology may be used, as the chemoreceptive control gates are added using postprocessing steps following fabrication of the CMOS circuitry.

Each transistor can have any number of normal control gates and chemoreceptive control gates, and the molecular/chemoreceptive properties of each such gate is separately tailorable. In operation, the chemoreceptive control gates are exposed to a fluid, such as a liquid or gas. The molecules present in such fluid adhere to the various chemoreceptive control gates, and charged groups on the molecules capacitively induce a charge on the floating gate. In further embodiments, the chemoreceptive control gates are replaced with photoreceptive control gates, or other sensor control gates having sensors with the capability of modifying capacitance in response to a sensed condition.

Figure 2:
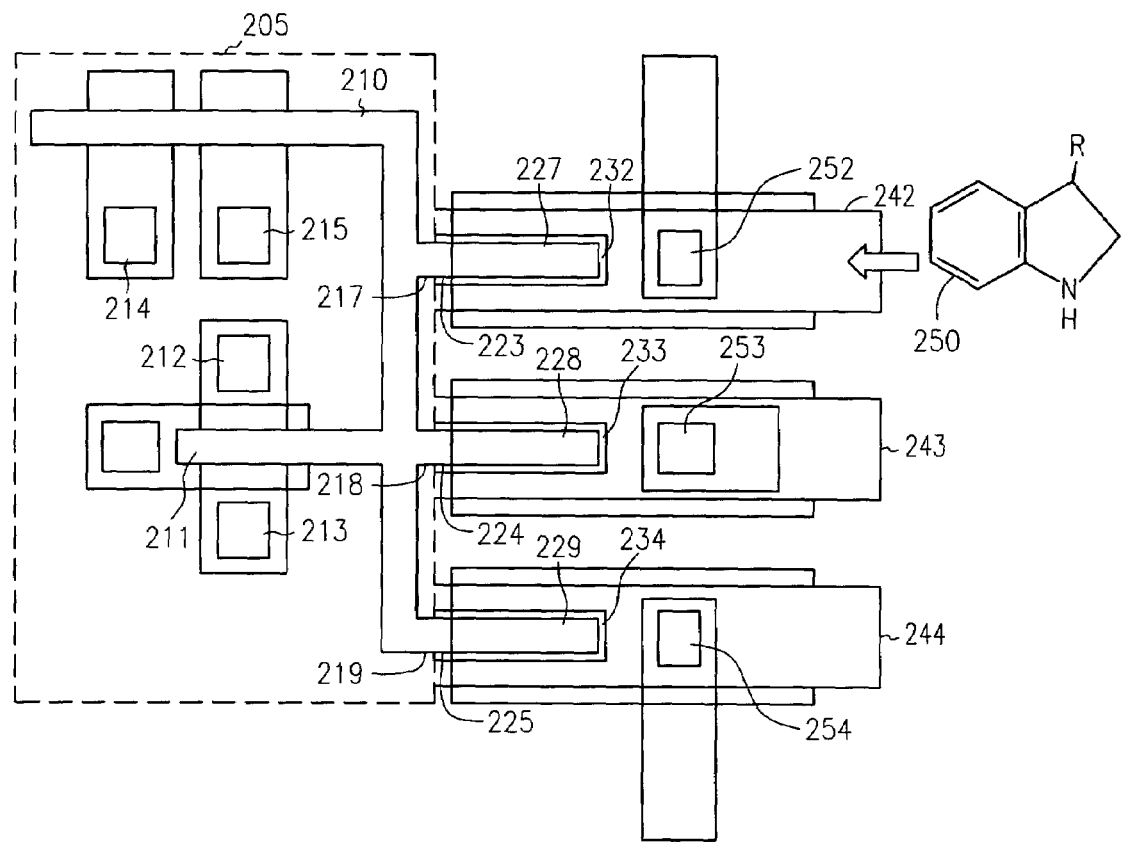
FIG. 2 is a plan view of a the transistor of FIG. 1 coupled to microfluidic fluid channels.

FIG. 2 is a plan view of a CvMOS transistor used in a sensor configuration for detecting molecules/chemicals. A broken line 205 is used to identify a floating gate MOS transistor having an extended gate structure 210. The transistor comprise a standard gate 211, source, 212, drain 213, and embedded floating gate structures 214, 215 for vMOS operations. Broken line 205 also represents a MOS window encapsulated from physical contamination. In one embodiment, the MOS transistor area has identical fabrication requirements with commercial Flash EEPROM.

The extended gate structure 210 is formed with three further extensions 217, 218, and 219 extending beyond broken line 205. An isolation area is formed at the end of each of the further extensions as indicated at 223, 224, and 225. In one embodiment, the isolation areas comprise nitride plugs. The nitride plugs serve as a dielectric between the further extensions, and corresponding fingers 227, 228 and 229. Each of the fingers is coated with a chemoreceptive layer 232, 233, and 234. The further extensions and corresponding fingers form electrodes of respective capacitors.

The fingers 227, 228, 229 are coupled to fluid by means of microfluidic channels 242, 243, and 244 to provide molecular and chemical samples in liquid or gas phase. The liquid phase involves the use of a buffer solution. The microfluidic channels deliver controlled sample molecules 250 with or without a buffer to the floating gate fingers with dielectric isolation and chemoreceptive coating that forms compact double layers (Helmholtz planes) with fluids. The channels may be independent for each finger, or may be coupled to form a chamber in one embodiment, such that multiple fingers are coupled to the same chamber. The areas and wall characteristics of the floating gate fingers determines the response signature for sensing selectivity. In one embodiment, different subthreshold slopes are used for different chemoreceptive coatings.

Si diffused resistors 252, 253, and 254 are provided with contacts in the channels for providing a reference potential to the microfluidic channels. The resistors can be coupled to further circuitry for processing. The sensor can perform selectivity analysis at the chip level without resorting to A/D conversion and further digital processing, and hence can have low power operations.

Figure 3:
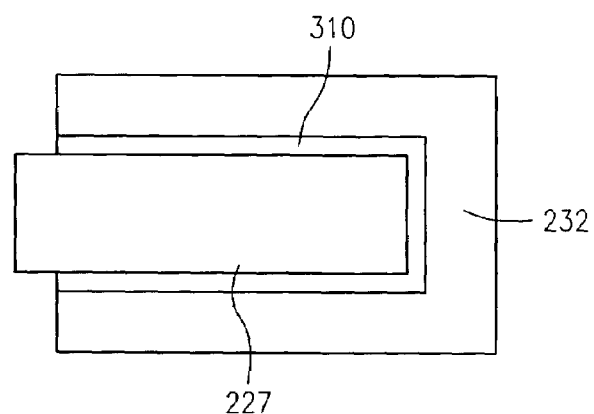
FIG. 3 is a plan view of a chemoreceptive control gate for the transistor of FIG. 1.

Further detail of finger 227 is shown in FIG. 3. The chemoreceptive layer 232 forms Helmholtz planes with the fluidic phase. Typical layers are receptive to polar gas, and liquids such as water and acetone. Many other types of layers are available and may be invented to be highly specific to other molecules/chemicals. Also more readily perceived in FIG. 3 is a thin dielectric isolation layer 310 disposed between the chemoreceptive layer 232 and the extended floating gate portion of finger 227. In one embodiment, this layer is approximately 2–6 nm thick, but may vary with different size sensors.

Figure 4:
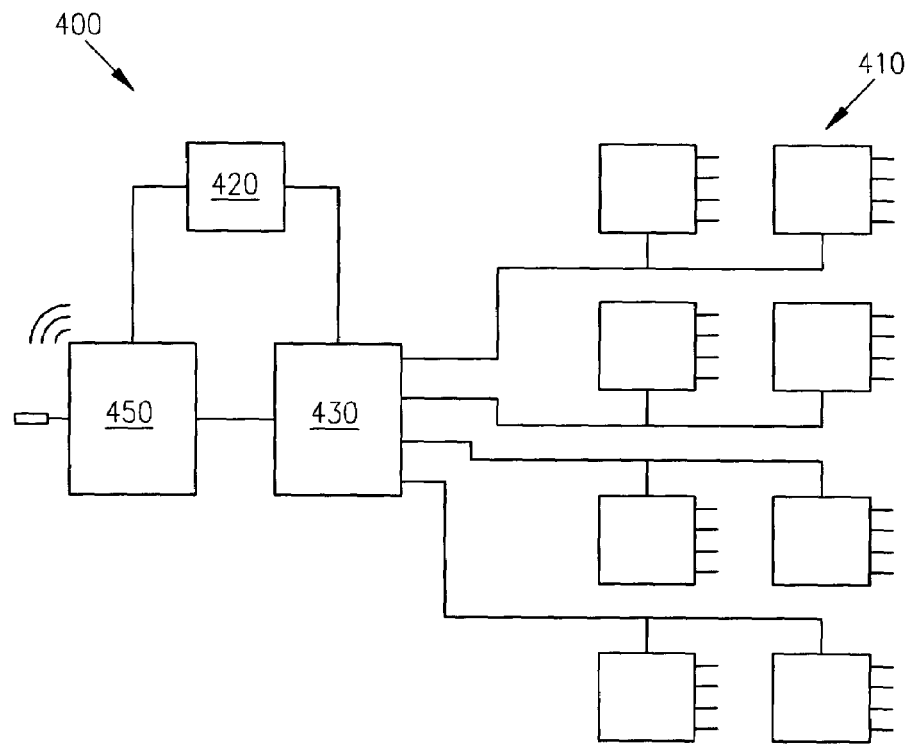
FIG. 4 is a block diagram view of an array of chemoreceptive control gate transistors.

FIG. 4 shows an array 400 of sensors 410 used for detecting multiple different chemicals/molecules. In one embodiment, each sensor comprises multiple fingers coated with the same receptive layer. Different sensors are used to detect different chemicals/molecules or other physical manifestations, and some sensors may be redundant. The array includes a power supply 420, such as a solar cell(s), battery, or transformer for coupling to an independent power source. A controller 430 is formed to implement functions of receiving signals from the multiple sensors and processing them to identify what is sensed. The array further includes a transponder 450 coupled to the controller for communicating results to other devices for further analysis. In one embodiment, the transponder comprises a RF or other electromagnetic based transponder. In further embodiments, the transponder comprises a modem, optical, or other electronic interface for communicating with other devices.

Figure 5:
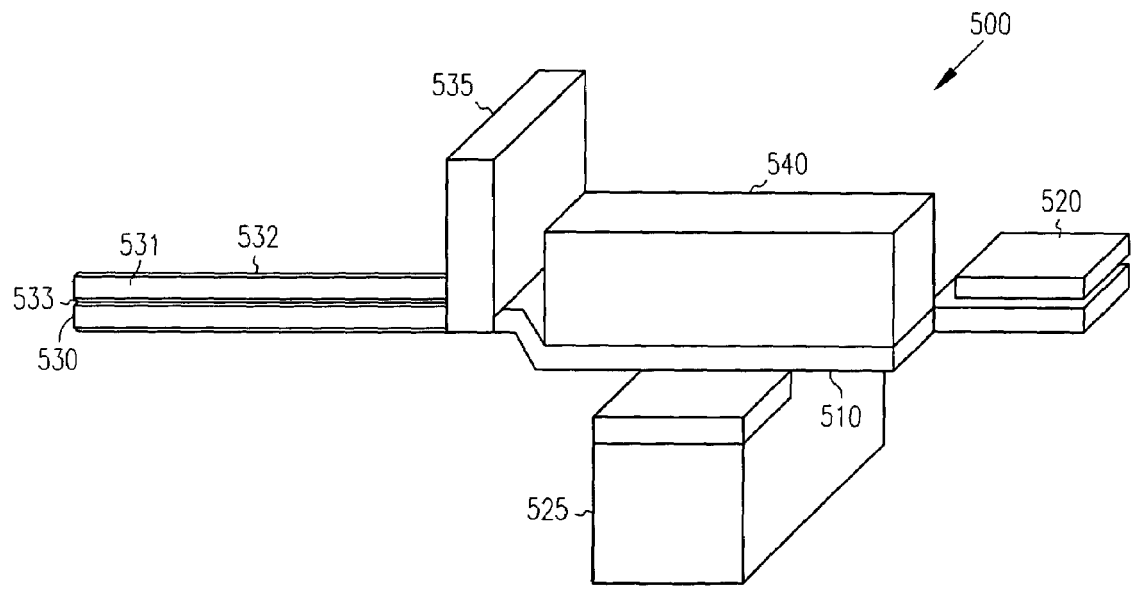
FIG. 5 is a block schematic diagram representing a further exemplary floating gate transistor having a chemoreceptive layer.

FIG. 5 shows an alternative chemoreceptive transistor 500. Transistor 500 comprises a source 510 and drain 515, and a gate 520 that modulates current flowing between the source and drain. Drain 515 is supported by a substrate 525. An extended floating gate 530 extends away from the drain 525.

In one embodiment, the extended floating gate 530 is formed of highly doped poly. A second highly doped poly layer 531 is separated from the first poly layer 530 by an inter-poly dielectric, such as an oxide 533. Oxide 533 is formed by chemical vapor deposition (CVD) of $SiO_2$ in one embodiment to a thickness of approximately between 10 and 40 nm. Other thicknesses may also be used.

In one embodiment, second poly layer 531 is referred to as a sensing gate. It may be covered with an oxide, and selected portions of the sensing gate are then exposed through an oxide etch. The exposed areas are then coated with a chemoreceptive material 532, while control gate 520 is a normal vMOS control gate. They chemoreceptive material 532 may be formed as a layer by dipping the floating gate in a poly solution. The chemoreceptive material is selective in one embodiment, such that a targeted chemical will bond with the material, creating a charge on the material that is capacitively coupled to the extended floating gate 530, thus affecting current flow through the transistor 500.

In one embodiment, an insulating structure 535 formed of oxide or other insulative material is positioned between the chemoreceptive surface 532 and the source 510 and drain 515. Source 510 is coated with a protective oxide 540 in one embodiment to keep the area physically and electrically isolated. Oxide that was formed on the floating gate is removed prior to coating the gate with the chemoreceptive material.

Figure 6:
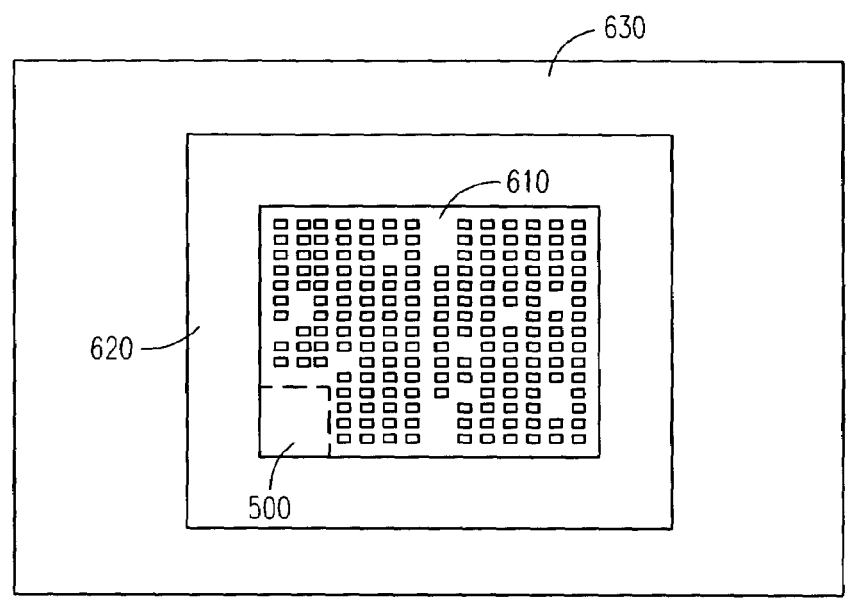
FIG. 6 is a perspective view of a CMOS chip incorporating a chemoreceptive transistor with a channel.

In a further embodiment, a further poly coating is applied over the chemoreceptive material and is patterned with microfluidic channels. Such channels are patterned as desired to provide fluid to the chemoreceptive material. Examples of such channels are shown in FIGS. 2 and 6. The channels in one embodiment are about 400 um thick.

FIG. 6 illustrates channels around a CMOS chip 610 with transistor 500 formed thereon. A microfluidic channel 620 for controlled fluid delivery to transistor 500 is formed by bonding a patterned silicone elastomer layer 630 on top of CMOS chip 610. The elastomer layer 630 obtains its pattern from curing on a master silicon die with features made by DRIE (Dry Reactive Ion Etching) or other suitable technique. In one embodiment, the height of fluidic channels is about 150 μm. The MOS chip may use fabrication processes similar to those used for commercial Flash memories, and therefore the chemoreceptive transistor is readily compatible with the conventional CMOS integrated circuitry. The modular structure of the extended sensing area with elastomer encapsulation confines the sample fluid delivery in the channel. It effectively eliminates possible contamination caused by the fluid to the gate oxide of the MOSFET.

Upon exposure of the extended floating gate polysilicon surface after the oxide etch on the sensing gates, four types of polymers are respectively used for the sensing-gate coating, as listed in Table 1, to enhance selective responses and provide versatile comparisons with the uncoated polysilicon surface.

TABLE 1

A list of polymers and the corresponding molecular weight for sensing-gate surface coatings:

| Polymer Coating | Molecular Weight |
| --- | --- |
| poly(vinyl acetate) | 90,000 |
| poly(vinyl butyral) | 100,000150,000 |
| poly(ethylene -co- vinyl acetate) | 72:28 (wt.) |
| poly(vinyl chloride) | 110,000 |

Coating solutions may be prepared at the room temperature. For poly(ethylene-co-vinyl acetate), 100 mg of the co-polymer is dissolved in 10 mL of benzene. For poly(vinyl acetate), poly(vinyl butyral), and poly(vinyl chloride), 20 mg of the polymer is dissolved in 10 mL of tetrahydrofuran (THF). After 10 to 15 minutes of mild agitation, the solution is visually inspected to ensure a proper mixture quality. The sensing area is then dipped into the solution to form a coating layer. After the solvent evaporates, a thin polymer layer is deposited on the sensing area. Other methods of applying the chemoreceptive layers may be utilized.

Figure 7:
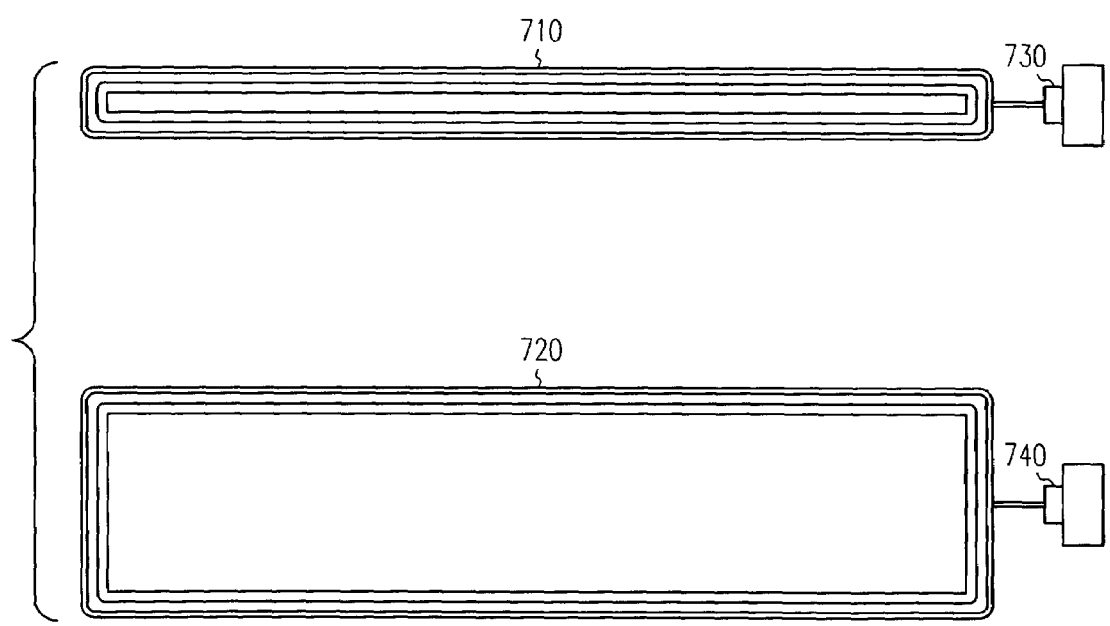
FIG. 7 is a block schematic diagram representing different width sensing gates.

Two different sensing gates are used in one embodiment to facilitate comparison, as illustrated in FIG. 7. A first sensing gate, gate 1 at 710 is narrow, and has a sensing area of 4.8×356.8 μm and a second sensing gate 2 at 720 is wide, and has a sensing area of 76.8×356.8 μm in one embodiment. The polysilicon of the sensing gate is electrically isolated from the polysilicon of the extended floating gate by an inter-poly oxide of about 58 nm as illustrated at 535 in FIG. 5 to create a parallel-plate capacitance. A gate oxide of the n-channel MOSFET is about 30 nm. In one embodiment, EEPROMs indicated at 730 and 740 are fabricated with the MOSFETs to record channel responses for later reading.

The individual thickness and roughness of example polymer coatings may be measured with a stylus-based surface profiler and are listed in Table 2. The arithmetical-mean roughness (Ra) and root-mean-square roughness (Rq) are calculated over about 100 μm on the wide sensing gate. Both Ra and Rq for the bare polysilicon surface are about 1 nm.

TABLE 2

The data of thickness and arithmetical mean roughness (Ra) for various polymer coatings.

| | | Roughness | |
| --- | --- | --- | --- |
| Polymer Coating | Thickness (nm) | Ra (nm) | Rq (nm) |
| poly(vinyl acetate) | 50 | 64 | 88 |
| poly(vinyl butyral) | 25 | 20 | 27 |
| poly(ethylene -co-vinyl acetate) | 30 | 2 | 2 |
| poly(vinyl chloride) | 30 | 8 | 13 |

Fluid provided by the channels interacts with the chemoreceptive surface through the formation of the electrical double layer at the solid-liquid interface. The capacitive load and static charges introduced onto the floating gate cause specific changes in both subthreshold slopes (S) and threshold voltages ($V_t$). Normalization may be used to eliminate parasitic deviations between devices. Measurements taken by measuring responses in deionized water or other desired fluids may be used to obtain information used to normalize the responses.

Figure 8:
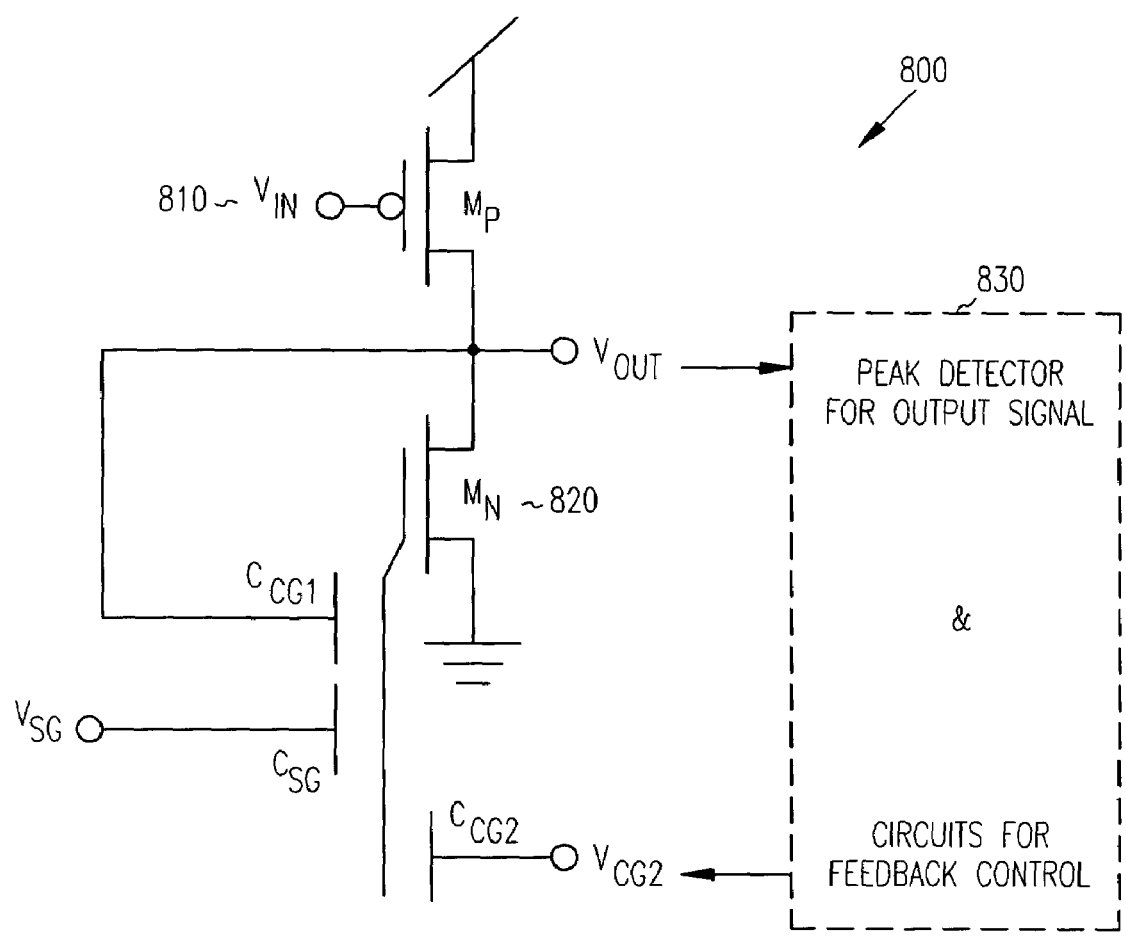
FIG. 8 is a circuit diagram showing circuitry for indicating subthreshold-slope variation.

To rapidly extract the information encoded in the form of subthreshold-slope variations on the sensing gates of the chemically receptive MOS (CvMOS) transistor, a simple circuit 800 of common-source amplification is used in one embodiment as shown in FIG. 8. An input signal $V_{in}$ 810 feeds into a gate 815 of a PMOS transistor 820, and is composed of a DC bias and an AC signal. The load of this common-source amplifier is the CvMOS transistor. Block 830 comprises a peak detector for the output signal, and circuits for feedback control.

The extended floating-gate structure capacitively monitors solid-liquid interaction at the sensing area, and also enables EEPROM electron tunneling operations, which provide additional degrees of freedom for the sensing mechanism. Comparisons of subthreshold-slope responses between the bare polysilicon surface and four different types of polymer coatings on the sensing gates indicate the selectivity of such devices can be significantly enhanced through a sensory array with versatile surface coatings, along with the charge control in the floating gate through electron-tunneling operations. Through the high transconductance gain of the MOS transistors, a high sensitivity can be derived, and the extraction of measured data can be realized by straightforward common-source amplifier circuitry.

I–V characteristics of the structure allow further utilization of specific adsorption to collect digitized information from multiple sensing gates. The multiple-input sensing structure may substantially reduce the need for digital-to-analog conversion (DAC) and digital signal-processing circuitry, and hence reduce the power consumption normally required for such sensor applications. Many different chemoreceptive materials may be used for specific-adsorption purposes. The thickness of such materials may be varied to provide different characteristics.

The invention claimed is:

1. A sensor comprising:
   a field effect transistor having a source, drain and floating gate, wherein the floating gate has an extended portion;
   a finger electrostatically coupled to the floating gate; and
   a chemoreceptive layer coupled to the finger.

2. A sensor comprising:
   a field effect transistor having a source, drain and floating gate, wherein the floating gate has an extended portion; and
   multiple chemoreceptive layers electrostatically coupled to the extended portion of the floating gate.

3. The sensor of claim 1 wherein the chemoreceptive layer is electrically isolated from the extended portion of the floating gate.

4. The sensor of claim 3 wherein the electrical isolation is provided by a nitride plug.

5. A sensor comprising:
   a field effect transistor having a source, drain and floating gate, wherein the floating gate has an extended portion; and
   multiple fingers capacitively coupled to the extended portion of the floating gate.

6. The sensor of claim 5 wherein some of the fingers comprise chemoreceptive layers capacitively coupled to the floating gate.

7. The sensor of claim 6 wherein a floating gate voltage is a weighted sum of voltages on the fingers.

8. The sensor of claim 7 wherein the weight on each control gate is directly proportional to the finger's capacitance, and is normalized by the total capacitance of the floating gate.

9. The sensor of claim 6 wherein the chemoreceptive fingers comprise a conductor and a film having chemoreceptive properties.

10. The sensor of claim 9 wherein the chemoreceptive fingers further comprises a dielectric isolator between the conductor and the chemoreceptive film.

11. A method of sensing comprising:
    providing a sample to multiple selectively receptive fingers to create a charge on the fingers;
    inducing a voltage on a floating gate capacitively coupled to the fingers as a function of the charge on the fingers; and
    modulating current through a source and drain based on the induced voltage on the floating gate.

12. A sensor comprising:
    a field effect transistor having a source, drain and floating gate, wherein the floating gate has an extended portion;
    a finger supported by the extended portion of the floating gate;
    a dielectric layer disposed between the extended portion of the floating gate and the finger; and
    a chemoreceptive layer supported by the finger.

13. The sensor of claim 12 and further comprising a microfluidic channel formed proximate the chemoreceptive layer that selectively provides fluid to the chemoreceptive layer.

* * * * *

UNITED STATES PATENT AND TRADEMARK OFFICE
CERTIFICATE OF CORRECTION

PATENT NO.      : 7,053,439 B2
APPLICATION NO. : 10/695432
DATED           : May 30, 2006
INVENTOR(S)     : Kan et al.

It is certified that error appears in the above-identified patent and that said Letters Patent is hereby corrected as shown below:

On the face page, in field (56), under "Other Publications", in column 2, line 11, delete "Immunienzymatic" and insert -- Immunoenzymatic --, therefor.

Signed and Sealed this

Twenty-sixth Day of September, 2006

JON W. DUDAS
*Director of the United States Patent and Trademark Office*